United States Patent [19]

Ito et al.

[11] 4,171,912

[45] Oct. 23, 1979

[54] ELEMENT ANALYZER EXPLOITING A MAGNETO-OPTIC EFFECT

[75] Inventors: Masaru Ito, Kodaira; Seiichi Murayama, Kokubunji, both of Japan

[73] Assignee: Hitachi, Ltd., Japan

[21] Appl. No.: 837,802

[22] Filed: Sep. 29, 1977

[30] Foreign Application Priority Data

Oct. 4, 1976 [JP] Japan .................................. 51/119209

[51] Int. Cl.² .............................................. G01J 3/42
[52] U.S. Cl. ..................................... 356/320; 356/312
[58] Field of Search .................................... 356/85–88, 356/93–97, 319, 320

[56] References Cited

U.S. PATENT DOCUMENTS 4,035,083   7/1977   Woodriff et al. ...................... 356/82

FOREIGN PATENT DOCUMENTS 2165106   7/1972   Fed. Rep. of Germany ............. 356/87

OTHER PUBLICATIONS

Uchida et al., *Oyo Buturi,* vol. 44, No. 8, Aug. 1975, pp. 852 (16)–857 (21).

*Primary Examiner*—F. L. Evans
*Attorney, Agent, or Firm*—Craig and Antonelli

[57] ABSTRACT

In an element analyzer exploiting a magneto-optic effect, when a concentration of the element in a sample material to be detected is high, two peaks are produced in the wave form of the signal obtained during the measurement. The present invention provides a discriminating technique to indicate whether two peaks appear in the wave form of the signal, with the object of reducing the error produced in the element analysis exploiting a magneto-optic effect.

7 Claims, 20 Drawing Figures

4,171,912

ELEMENT ANALYZER EXPLOITING A MAGNETO-OPTIC EFFECT

FIELD OF THE INVENTION

The present invention relates to a quantitative analyser of an element which has exploited a magneto-optic effect and provide an apparatus having a means for discriminating the wave form of the measurement signal.

DESCRIPTION OF THE PRIOR ART

In the scattering of light by randomly distributed atoms, it is known that, in the case where the scattered light wavelength does not differ before and after the scattering and where the scattering direction is identical to the propagating direction of the incident light (that is, the scattering is forward scattering), said scattering is a coherent phenomenon, and if the number of atoms is small so as to permit one to ignore the light absorption by atoms, the scattered light intensity will be proportional to the square of the number of atoms involved in the scattering. On the other hand, the intensity of light scattered in any direction other than the aforecited one is directly proportional to the number of the atoms involved in the scattering. Therefore, if forward scattering is employed, stronger light scattering can be obtained. Further, it is known that, in the case of resonance scattering where the wavelength of the incident light is coincident with the resonance wavelength of the atoms, the scattered light intensity becomes very much higher than the case where the respective wavelengths are not coincident.

Since the resonance wavelength is an indication of the identify of the element, it is possible to identify an element according to the detected resonance wavelength thereof. Accordingly, it is possible to perform a highly sensitive element analysis by employing forward resonance scattering.

Figure 1:
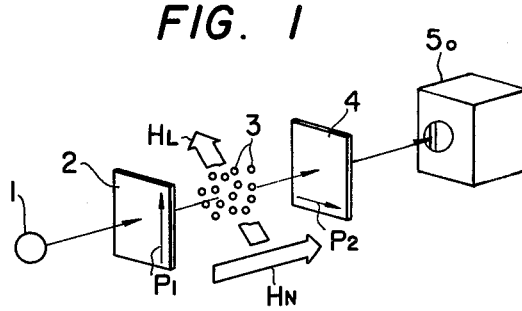
FIG. 1 is a diagrammatic view illustrating the principle of measurement adapted by this invention based on a magneto-optic effect.

The principle of measurement exploiting a magneto-optic effect is illustrated in FIG. 1. Light emergent from a light source, which has a spectral distribution including the resonance wavelength of the atoms to be detected, is converted by the polarizer 2 into linearly polarized light having a polarization direction $P_1$. This linearly polarized light is incident upon the atomic vapor 3 and scattered. An external magnetic field $H_N$ (in parallel to the optical path) or $H_1$ (transverse to the optical path) is applied to the atomic vapor 3. According to the magneto-optic effect produced by the above operation, the polarization state of the scattered light is different from the polarization state of the incident light.

Figure 2:
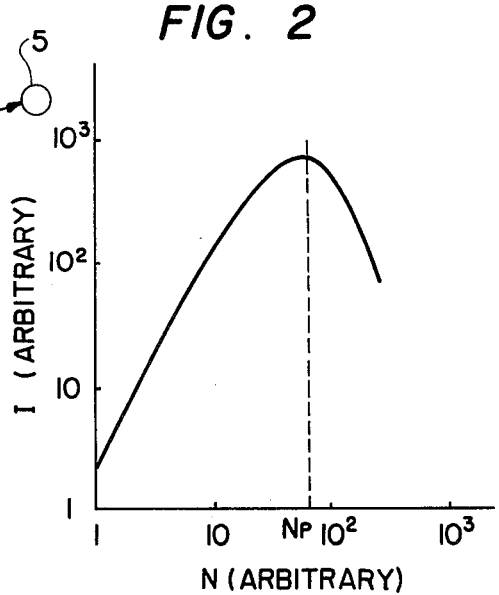
FIG. 2 is a diagram illustrating the relation between the intensity of a transmitted light signal I and the density N of atoms in an element analysis method exploiting a magneto-optic effect.

The light transmitted through the atomic vapor, that is, the forward scattered light, and the incident light, is introduced into the analyser 4. Only the forward scattered light component which has a polarization direction $P_2$ perpendicular to the incident polarization direction $P_1$ passes through the analyzer 4, and only the light component having the resonance wavelength of atoms passes through the spectrometer $5_0$, and is detected by the detector 5. The relation between the intensity of the transmitted light and the number density of atoms involved in the sample has been examined already and reported in "Proceeding of Royal Society of London" vol. A293, page 70, 1966, by A. Corney, B. P. Kibble and G. W. Series. According to their theory, the above mentioned relation is calculated and illustrated typically in FIG. 2. According to this result, we realize that if the number density N of atoms involved in a sample is low, the intensity of the transmitted light I is proportional to the square of the number of atoms involved in the scattering, and in the case where the number density N of atoms becomes great, the intensity of the transmitted light I is saturated and reaches a maximum value at Np. Further as the density N becomes greater than Np, the intensity I is reduced owing to the self absorption of the atoms.

Figure 3:
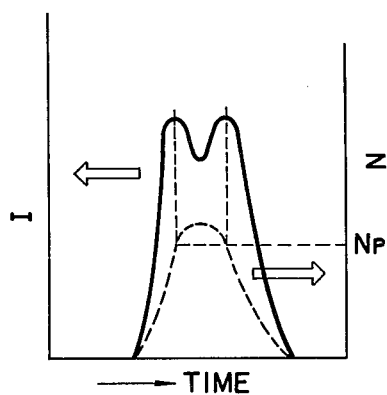
FIG. 3 is a diagram illustrating the relation between the generating atomic vapor density N and the intensity the transmitted signal I with lapse of time in the case of the concentration of the element involved in a sample.

The thermal decomposition method is one of the available methods of producing the atomic vapor. In atomic absorption and atomic fluorescence methods of analysis, a flameless method of thermal decomposition is selection from various thermal decomposition methods for its high detection sensitivity. If such a method of producing the atomic vapor is employed, in the case of the high concentration of the objective atoms involved in a sample, a wave form of the signal intensity I as shown by the solid line in FIG. 3 is obtained. That is, a dip is generated in said wave form of the signal, and the signal has two peaks. The number density of the atoms in accordance with this wave form of the signal is shown by the dashed line in FIG. 3. As shown in FIG. 3, the number density of the atoms increases with lapse of time, at a specific time it reaches a maximum value, and after that its value tends to decrease. In the case where the maximum value of the number density of the atoms generated from a sample is greater than the saturated value of the number density of atoms Np, the number density of the atoms becomes equal to Np at least at two separate instants. Since at this instant the intensity of the signal I reaches its peak value, a signal having two peaks is obtained.

However, in many cases, analytical works are routine works, and in the course of the element analysis such a wave form is not always noted. That is, in the element analysis a peak value or a signal value integrated with time is indicated by the indicator or printed out, and an analyst reads out only the integrated value. From the high concentration sample of which the signal has two peaks, one can obtain only the one highest peak value, so that one normally does not know whether this sample produces a signal having two peaks or not. An accurate measurement of element concentration in a sample can not be done in such case. Further, in the signal integration method, in spite of the high concentration of elements its integrated value becomes small, and therefore, cannot provide an exact analysis.

SUMMARY OF THE INVENTION

The present invention may be employed to distinguish between a signal having two peaks and a signal having one peak, which signals are emergent from the prior art element analyser exploiting a magneto-optic effect.

The present invention provides a magneto-optic element analyser including a space for a sample material; means for applying a magnetic field to said sample material; a light source arranged on the optical axis; a polarizer arranged on the optical axis between the said electromagnetic radiation source and the said space for the sample material; an analyzer arranged on the optical axis next to the space for a sample material disposed on the side of said space opposite that on which said polarizer is arranged; spectro analysing means is arranged on the optical path of the optical beam emergent from the said analyzer through the space for the sample material; a detector for detecting light emergent from a exit slit of the said spectro analysing means; and means for distinguishing between two peaks and a single peak in the wave form of the signal obtained in the output of said detector.

In accordance with the present invention, the distinction between two peaks and a single peak of the wave form of the signal produced in the photo-detector is effected with a high sensitivity, and accordingly, the analysis may be accurately done.

DESCRIPTION OF THE PREFERRED EMBODIMENTS

Hereinafter, the present invention will be described in detail in conjunction with various preferred embodiments. The following embodiments will be described only with respect to the signal processing circuit of the detector. The principal part of the element analyser is constituted by a space for a sample material arranged on an optical axis; means for applying a magnetic field to the said sample material; a light source arranged on the optical axis; a polarizer arranged on the optical axis between the said light source and the said space; an analyzer arranged on the optical axis next to the said space on the opposite side of said polarizer; a spectrometer arranged on the optical axis next to the said analyzer on the opposite side of said space; a photo detector for detecting light emerging from the said spectrometer as shown in FIG. 1.

Figure 4:
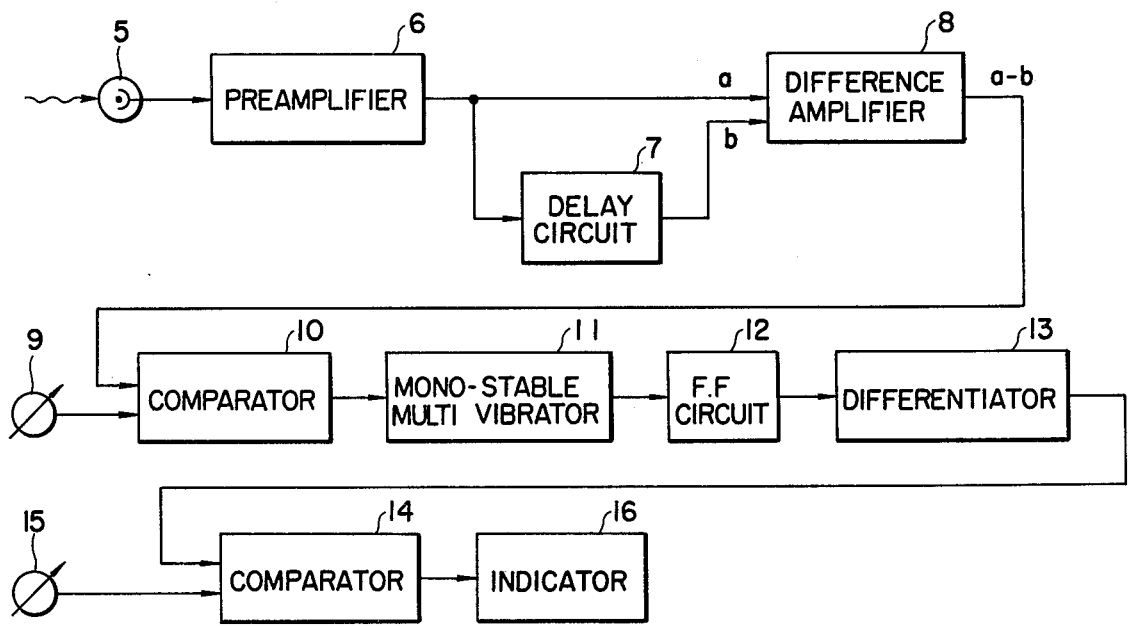
FIG. 4 is a block diagram of one embodiment of a signal discrimination circuit employing the element analyser of the present invention.

FIG. 4 is a block diagram of the present invention employed to distinguish between a two-peak signal and a single-peak signal. A signal light is converted to a electric signal by a photodetector 5, thereafter the said electric signal is amplified to a suitable intensity by a preamplifier 6, and further the said electric output signal is split into two electric signals a and b, one signal output b being delayed for a required time through a delay circuit 7 with respect to the other signal output a. The signal a obtained directly from preamplifier 6 and the signal b delayed with respect to the signal a through a delay circuit 7 are introduced into a differential amplifier 8, and the difference between these signals is taken by said differential amplifier 8. Subsequently the output signal obtained from said differential amplifier 8 is compared with a standard voltage 9 by a comparator 10. If the said signal from the differential amplifier is greater than the standard voltage, then a constant voltage is obtained from said comparator 10.

This output signal is converted into an electric pulse having a constant time width by a mono-stable multivibrator 11, the pulse is introduced into a flip-flop circuit 12, the output of flip-flop 12 is differentiated by a differentiator 13, this differentiated output is compared with a second standard voltage 15 by a comparator 14, and when the derived value has a magnitude greater than the standard voltage, an output pulse is produced. This output pulse is indicated by an indicator 16. The circuit made up of the elements from comparator 10 to indicator 16 is a counting circuit having a pulse of constant sign (positive or negative). Only when more than two constant sign pulses produced by this counting circuit will indicator 16 operate.

Figure 5A:
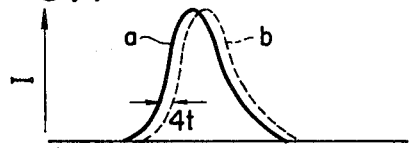
FIGS. 5A–5D are diagrams showing the wave form of the signal derived in a signal discrimination circuit such as shown in FIG. 4.
Figure 5B:
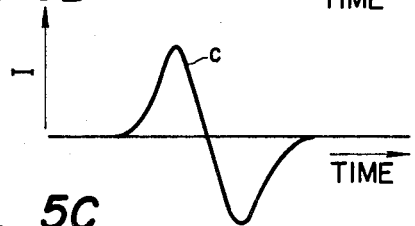
Figure 5C:
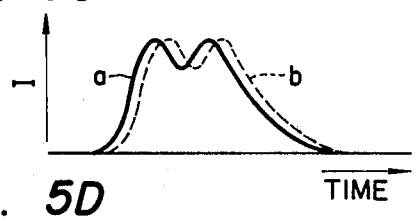

The mode of a signal in this signal discriminating circuit is shown in FIGS. 5A–5D. FIG. 5A shows a signal a and a signal b, when the output of the photodetector is a single peak signal. Signal b is delayed for Δt with respect to signal a by the delay circuit 7. The curve C in FIG. 5B represents an output signal from differential amplifier 8. In this case the output signal a–b has only one pulse of a given polarity; for example, only one pulse of positive sign is produced. On the other hand, when the output signal from differential amplifier 8 has two peaks, the forms of signal a and of signal b are shown in FIG. 5C. The output signal a–b from the differential amplifier is shown by the curve d in FIG. 5D. Pulses of positive sign appear twice in this case. Of course, in the case of a multiple peak signal, the positive pulses appear as same times as the number of peaks in said signal. And thereafter, the number of this positive sign pulse is counted by the signal discriminating circuit, as shown in FIG. 4, in the section from the comparator 11 to the indicator 16. When the number of this positive sign pulse is greater than two, this state is indicated.

Figure 6:
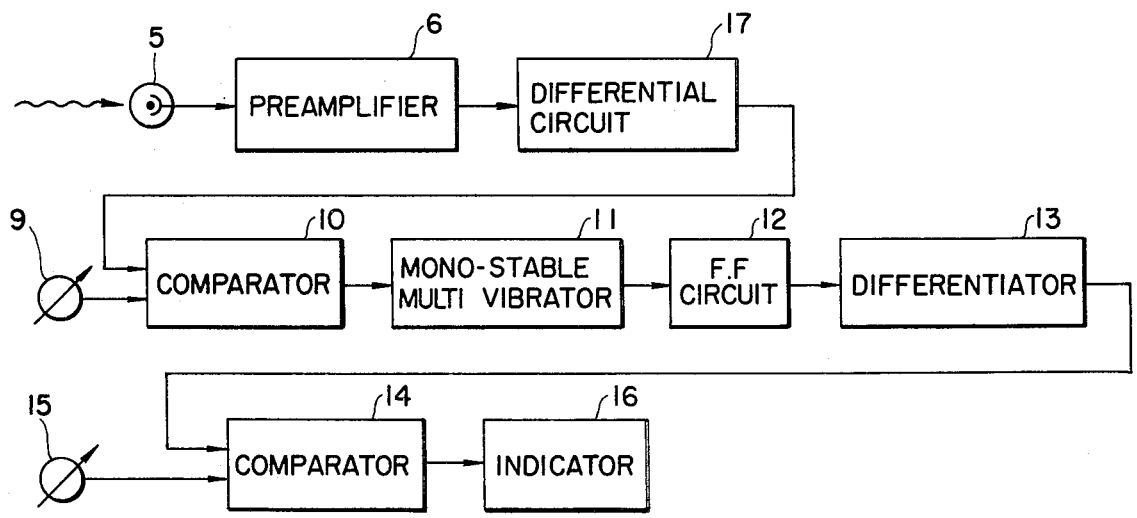
FIG. 6 is a block diagram of a second embodiment of a signal discrimination circuit employing the element analyser of the present invention.

FIG. 6 is another signal discriminating circuit according to this invention. The signal is converted into an electric signal by a photo-detector 5, and is differentiated by a differentiation circuit 17 after being amplified to a proper level by a preamplifier 6. Thereafter, this signal is compared with a standard voltage 9 by a comparator 10, and when the signal has greater value than the standard voltage, a signal output of constant voltage value is derived from the comparator. In this signal discriminating circuit, the circuit from the comparator 10 to the indicator 16 is the same circuit as shown in FIG. 4. In a differentiation process, noise components are also differentiated, and contribute to great noise. Therefore, a filter having a proper time constant is required for the preamplifier 6, and the standard voltage 9 is required to set a suitable level.

FIG. 7 shows the mode of the signal, when the differentiation circuit is employed in the signal processing circuit.

Figure 5D:
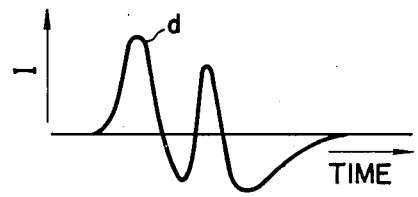
Figure 7A:
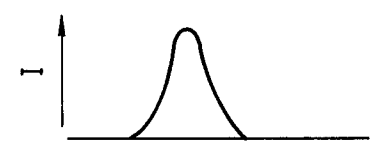
FIGS. 7A–7D are diagrams showing the wave form of the signal derived in a signal discrimination circuit such as shown in FIG. 6.
Figure 7B:
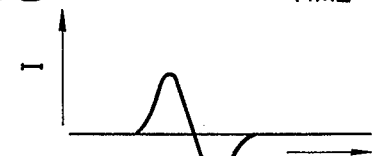
Figure 7C:
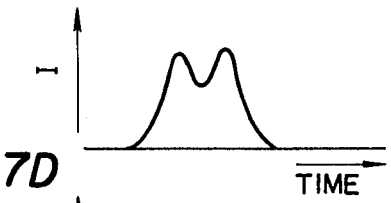
Figure 7D:
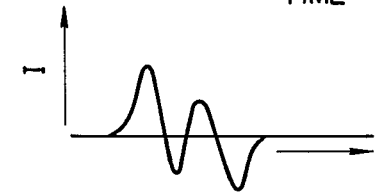

When the output signal from the detector 5 has a single peak as shown in FIG. 7A, and the output from the differentiation circuit 17 is as shown in FIG. 7B, only one positive pulse is obtained. When the output signal from the detector 5 has two peaks as shown in FIG. 7C, the output from the differentiation circuit 17, as shown in FIG. 7D, will have two positive pulses in the same manner as shown in FIG. 5D.

Figure 8:
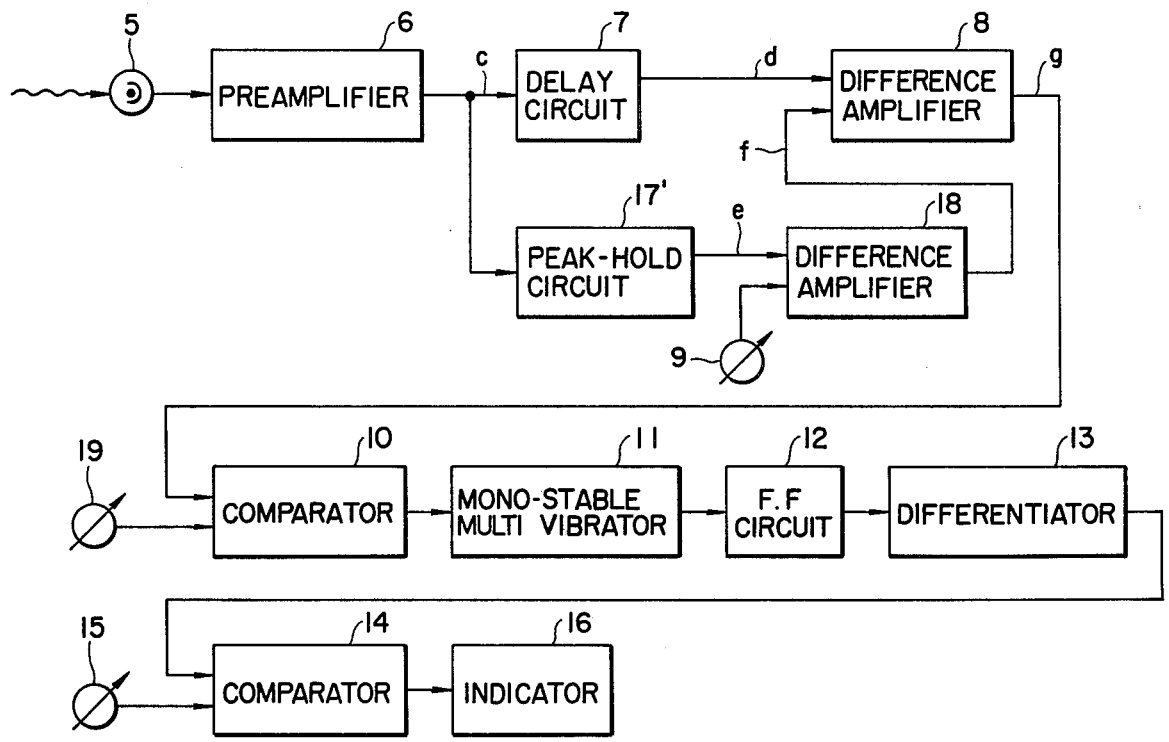
FIG. 8 is a block diagram of another embodiment of a signal discrimination circuit employing the element analyser of the present invention.
Figure 9A:
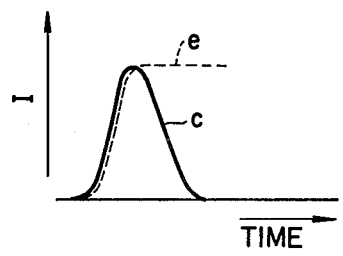
FIGS. 9A–9F are diagrams showing the wave form of the signal derived in a signal discrimination circuit such as shown in FIG. 8.
Figure 9D:
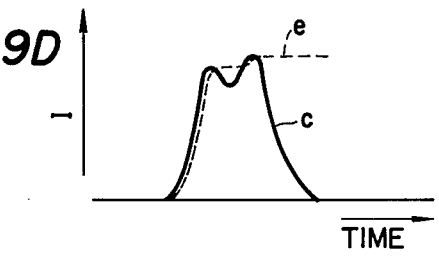
Figure 9B:
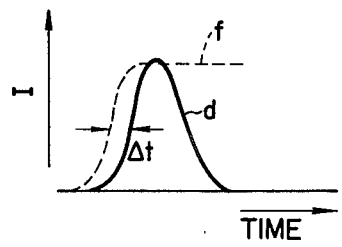
Figure 9E:
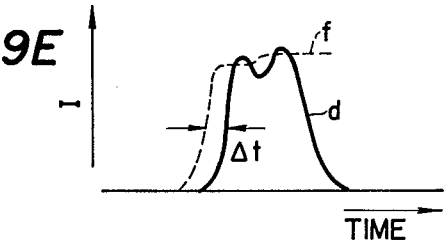
Figure 9C:
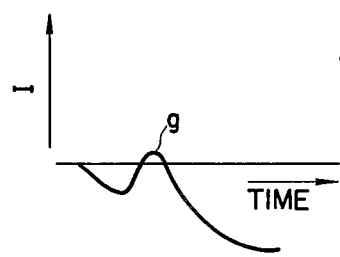
Figure 9F:
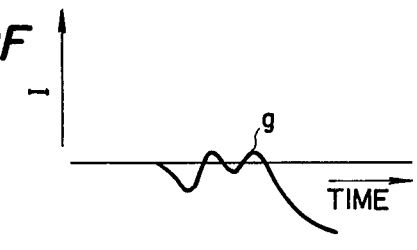

FIG. 8 shows a signal discriminating circuit according to another embodiment of the present invention. The signal is converted to an electric signal by the detector 5, and the said signal is amplified to a suitable level by the preamplifier 6. Further, the amplified signal C is split into two electric signals. The one signal d is delayed by the delay circuit 7, and the other signal e is made to hold the maximum value of the signal c by the peak-hold circuit 17'. Further the difference between the said signal e and the standard voltage 9 is obtained by a differential amplifier 18, that is, the level of the signal e is slightly lowered, to produce the signal f at the output of amplifier 18. The difference between this signal d and signal f is produced by a differential amplifier 8, and becomes the signal g. This signal g is compared to the second standard voltage 19, and when the said signal g is greater than the said standard voltage, a constant voltage output is derived from the comparator 10. In this signal discriminating circuit of FIG. 8, the circuit from comparator 10 to indicator 16 is the same circuit as shown in FIG. 4, that is a number of pulses of a required sign, for example a number of positive sign pulses is counted, and the result is indicated. FIGS. 9A-9F illustrate the form of the signal in the case of employing the signal discriminating circuit shown in FIG. 8. In the case where the signal c has a single peak, the peak holded signal e is a dashed line in FIG. 9A. Then, the signal c is delayed for a time Δt, and becomes the signal d, while the signal e is slightly lowered in level by differential amplifier 18, and becomes signal f, as seen in FIG. 9B. The difference between this signal d and signal f is obtained by a differential amplifier 8 again, and results in signal g. In this case, there is only one positive pulse, as seen in FIG. 9C. In the case where a detected signal c shows two peaks, for example as seen in FIG. 9D, the case where the height of the latter peak is higher than the former peak, the peak-hold signal e turns into a step wise signal. The signal c is delayed for a time Δt, and becomes signal d, while the peak-hold signal e is slightly lowered, and becomes signal f as seen in FIG. 9E. The difference between the signal d and the signal f results in a curve g, as shown in FIG. 9F. In the case where the signal c has two peaks, the curve g has two positive pulses. The number of positive pulses is counted, and it is distinguished whether the signal C has a single peak or two peaks.

As described above, in accordance with the present invention, it is easy to distinguish between a two-peak signal and a single-peak signal obtained by the detector, therefore, the analyst can analyze easily and accurately the concentration of elements in the sample, in accordance with the present invention, after the detecting signal is converted into a pulse having the required sign. Other generally familiar signal processing technique may as well be employed to count the number of this pulse having a required sign. Moreover, the indicator may take the form of a lamp or a buzzer producing a warning signal, and it is also possible to design the system so as to generate a reset signal of the measurement operation in the case where the signal has two peaks.

We claim:

1. An element analyzer exploiting a magneto-optic effect comprising:
   a space for a sample material, means for applying a magnetic field to said sample material,
   a light source arranged on an optical axis,
   a polarizer arranged on the optical axis between said light source and said space for said sample material,
   an analyzer arranged on the optical axis next to the space for said sample material and disposed on the side of said space opposite that on which said polarizer is arranged,
   spectro analyzing means arranged on the optical path of the light emergent from said analyzer which acts on the light which has passed through said space for the sample material, and
   detector means for detecting light emergent from said spectro analyzing means, including a detector for detecting the light and means for discriminating between a signal obtained at the output of said detector having a single peak and a signal having multiple peaks.

2. An element analyser according to claim 1 wherein said discriminating means includes means for splitting the output signal derived from said detector into first and second signals, delay means for delaying said first signal with respect to said second signal, a differential amplifier receiving said delayed first signal and said second signal, and means for counting the number of pulses of a given polarity emergent from the output of said differential amplifier.

3. An element analyser according to claim 1, said discriminating means includes a differentiation circuit connected to receive the output of said detector, and means for counting the number of pulses having a required sign emergent from the output of said differentiation circuit.

4. An element analyser according to claim 1, said discriminating means includes means for splitting the output signal obtained from the output of said detector into first and second signals, a delay circuit, a first differential amplifier receiving said first signal through said delay circuit, a peak-hold circuit connected to receive said second signal, a second differential amplifier having one input connected to the output of said peak-hold circuit and a second input connected to a standard voltage to obtain the difference therebetween, the output of said second differential amplifier being applied to said first differential amplifier, and means for counting the number of peaks having a required sign which emergent from the output of said first differential amplifier.

5. An element analyser according to claim 2 wherein said counting means includes a first comparator receiving the output of said differential amplifier and a first reference voltage source, a monostable multivibrator connected to the output of said first comparator, a flip-flop circuit connected to the output of said multivibrator, a differentiator connected to the output of said flip-flop circuit, a second comparator receiving the output of said differentiator and a second reference voltage, and an indicator connected to the output of said second comparator.

6. An element analyser according to claim 3 wherein said counting means includes a first comparator receiving the output of said differentiation circuit and a first reference voltage source, a monostable multivibrator connected to the output of said first comparator, a flip-flop circuit connected to the output of said multivibrator, a differentiator connected to the output of said flip-flop circuit, a second comparator receiving the output of said differentiator and a second reference voltage, and an indicator connected to the output of said second comparator.

7. An element analyser according to claim 4 wherein said counting means includes a first comparator receiving the output of said first differential amplifier and a first reference voltage source, a monostable multivibrator connected to the output of said first comparator, a flip-flop circuit connected to the output of said multivibrator, a differentiator connected to the output of said flip-flop circuit, a second comparator receiving the output of said differentiator and a second reference voltage, and an indicator connected to the output of said second comparator.

* * * * *